United States Patent
McEwen

(10) Patent No.: US 7,901,676 B2
(45) Date of Patent: Mar. 8, 2011

(54) THERAPEUTIC COMPOSITION FOR THE TREATMENT OF RHEUMATOID ARTHRITIS

(75) Inventor: Simon McEwen, Pangbourne (GB)

(73) Assignee: Epidyme Limited, Berkshire (GB)

( * ) Notice: Subject to any disclaimer, the term of this patent is extended or adjusted under 35 U.S.C. 154(b) by 670 days.

(21) Appl. No.: 10/820,099

(22) Filed: Apr. 7, 2004

(65) Prior Publication Data
US 2004/0228850 A1 Nov. 18, 2004

(30) Foreign Application Priority Data
Apr. 7, 2003 (GB) .................................. 0307989.4

(51) Int. Cl.
*A61K 38/47* (2006.01)
*A61K 38/00* (2006.01)
(52) U.S. Cl. ..................... 424/94.61; 435/200; 530/356; 514/2
(58) Field of Classification Search ............... 424/94.61; 435/200; 530/356; 514/2
See application file for complete search history.

(56) References Cited

U.S. PATENT DOCUMENTS

| | | | |
|---|---|---|---|
| 4,510,129 A | 4/1985 | Knop et al. | |
| 5,268,463 A * | 12/1993 | Jefferson | .................... 536/23.7 |
| 6,162,787 A | 12/2000 | Sorgente et al. | |
| 2001/0056069 A1 * | 12/2001 | Klaus | .......................... 514/21 |
| 2003/0118672 A1 * | 6/2003 | McPeak et al. | ............. 424/750 |
| 2006/0024334 A1 * | 2/2006 | Larche et al. | ............ 424/275.1 |
| 2008/0314333 A1 * | 12/2008 | Hurwitz | ....................... 119/709 |

FOREIGN PATENT DOCUMENTS

| | | |
|---|---|---|
| EP | 1 228 767 A | 8/2002 |
| GB | 2205746 A | 12/1988 |
| IT | 1218080 | 4/1990 |
| WO | WO 94/07520 A1 | 4/1994 |

OTHER PUBLICATIONS

Derwent patent abstract for JP 52076416A (1977), downloaded from WEST on Jul. 29, 2007 (1 page).*
Terr, A. "Unproven and Controversial Forms of Immunotherapy" Clinical Allergy arid Immunol. (Dekker: NY, NY) (1999) 12: 479-488.*
Terr, A. "Unproven and Controversial Forms of Immunotherapy" Clinical Allergy and Immunol. (Dekker: NY, NY) (2004) 18: 703-710.*
The Merck Manual of Diagnosis and Therapy Berkow, Ed. (1987) (Merck Sharp & Dohme Research Laboratories: Rahway, NJ) p. 949-973.*
Nemeth-Csoka et al. Frenius Zeitschrift fuer Analytisch Chemie (1984) 317(6): 690-2.*
Jebens et al. J. Bone and Joint (1959) 418: 388-400, abstract.*
Houli et al. Arquivos Interamericanos de Rheuatologia (1959) 2: 48-65, abstract.*
Worth, J. (2001) www.talkeczema.com/webdocs/features/feature_epd.php; 8 pages; down-loaded on Feb. 5, 2010.*
Jacox et al. J. Clin. Investigation (1955) 34: 263-7.*
Annals of Allergy (1975), vol. 35(2), pp. 98-103, "Enzyme potentiated hyposensitization: V . . . ", McEwen; see whole document.
Annals of Allergy (1975), vol. 34(5), pp. 290-295, "Enzyme potentiated hyposensitization: IV . . . ", McEwen et al; see "Method".
Cantani, et al., "Enzyme-Potentiated Desensitization in Children with Asthma and Mite Allergy: A Double-Blind Study", Journal of Investigational Allergology and Clinical Immunology, 6(4):270-276, 1996.
Egger, et al., "Controlled Trial of Hyposensitization in Children with Food-Induced Hyperkinetic Syndrome", Lancet 339(8802):1150-1153, 1992.
McEwen, et al., "Enzyme-potentiated Hyposensitization. 3. Control by Sugars and Diols of the Immunological Effect of Beta Glucuronidase in Mice and Patients with Hay Fever", Annals of Allergy 31(11):543-550, 1993.
Menge, et al., "Monoclonal Autoantibodies from Patients with Autoimmune Diseases: Specificity, Affinity and Crossreactivity of Mabs Binding to Cytoskeletal and Nucleolar Epitopes, Cartilage Antigens and Mycobacterial heat-Shock Protein 60", Immunobiology 205(1):1-16, 2002.
Wang, et al., "The influence of HLA-DR4 (0401) on the immune response to type 11 Collagen and the Development of Collagen Induced Arthritis in Mice", Journal of Autoimmunity 18(2):95-103, 2002.
Matteson, E.L., Current Treatment Strategies for Rheumatoid Arthritis: Mayo Clinic Proceedings, Mayo Medical Ventures 75(1):69-74, 2000.
Vischer, T.L., "Oral Desensitization in the Treatment of Human Immune Diseases" Zeitschrift Fuer Rheumatologie, 54(3):155-157 1995.
Targoni, et al., "Prevention of Murine EAE by Oral Hydrolytic Enzyme Treatment" Journal of Autoimmunity, 12(3):191-198 1999.
Shrader, Jr., W.A. et al. "Enzyme Potentiated Desensitization (EPD)"White Paper for United States Senators and Representatives, The American EPD Study: 1993-2000, Sep. 2001 revised Oct. 15, 2001, pp. 1-14.
Astarita et al., "Effects of Enzyme-Potentiated Desensitisation in the Treatment of Pollinosis: A Double-Blind Placebo-Controlled Trial", J. Invest. Allegol. Clin. lmmunol,. (1996) 6(4):248-55.
Fell et al., "A Single Dose Desensitization for Summer Hay Fever", Eur. J. Clin. Pharmacol. (1990) 38:77-79.

(Continued)

Primary Examiner—Irene Marx
Assistant Examiner—Susan Hanley
(74) Attorney, Agent, or Firm—Edwards Angell Palmer & Dodge LLP; Peter C. Lauro, Esq.; Melissa Hunter-Ensor, Esq.

(57) ABSTRACT

A therapeutic composition and a method for rheumatoid arthritis is described. The composition comprises purified beta-glucuronidase at a concentration of between 200 and 10,000 Fishman units/ml and purified collagen at a concentration of between 0.5 and 2.5 mg/ml. The composition is administered by transdermal infusion or intradermal injection.

16 Claims, 2 Drawing Sheets

OTHER PUBLICATIONS

Hershkoviz et al., "Keratinocytes-Associated Chemokines and Enzymatically Quiescent Heparanase Induce the Binding of Resting CD4+ T Cells." *J. Invest. Dermatol.* (1996) 106(2):243-8.

Ho, K.J., "Activation of Human β-glucuronidase by Murine Monoclonal Antibodies and Bovine Serum Albumen", *Biochem. MI. Biol. Int.* (1995) 36(6):1277-86.

Ippoliti et al., "Effect of Preseasonal Enzyme Potentiated Desensitisation (EPD) on Plasma-IL-6 and IL-10 of Grass Pollen-Sensitive Asthmatic Children", *Allerg Imrnunol*, May 1997;29(5):120, 123-5.

Kondo et al., "Interleukin-10 Inhibits the Elicitation Phase of Allergic Contact Hypersensitivity", *J. Invest. Dermatol.*, (1994) 103:811-4.

Longo et al., "[Clinical Efficacy of a new Syposensitising Treatment, EPD (Enzyme Potentiated Desensitization) in the Therapy of Pollinosis]", *Riforma Med.*, (1992) 107:171-6.

McEwen et al., "Hyaluronidase in the Treatment of Allergy", *Brit Med. J.*, (1967) ii:507-508.

McEwan, L.M., "Effects of Sugars and Dials on Enzyme-Potentiated Hyposensitization", *J. Physiol*, (1972) 230:65-66.

McEwen et al., "Enzyme Potentiated Hyposensitisation I: The Effect of Pre-Treatment with βglucuronidase, Hyaluronidase, and Antigen on Anaphylactic Sensitivity of Guinea-Pigs, Rats and Mice", *Int. Arch. Allergy* (1972) 42:152-8.

McEwen, L.J., "Enzyme Potentiated Hyposensitization II: Effects of Glucose, Glucosamine, N-acetylamino Sugars and Gelatin on the Ability of βglucuronidase to Bock the Anamnestic Response to Antigen in Mice", *Annals of Allergy*, (1973) 31:79-83.

McEwen, L.M., "A Double-Blind Controlled Trial of Enzyme Potentiated Hyposensitization for the Treatment of Ulcerative Colitis", *Clin. Ecol.* (1987) 5(2):47-51.

Pipe, R.K., "Hydrolytic Enzymes Associated with the Granular Haemocytes of the Marine Mussel *Mytuslis edulis*", *Histochemical J.* (1990) 22:595-603.

\* cited by examiner

THERAPEUTIC COMPOSITION FOR THE TREATMENT OF RHEUMATOID ARTHRITIS

This application claims priority to British patent application GB0307989.4 filed Apr. 7, 2003, the disclosure of which application is incorporated herein in its entirety by this reference. The contents of all patents, patent applications, and references cited throughout this application are hereby incorporated by reference in their entireties.

This invention relates to a therapeutic composition. More particularly, the present invention relates to a therapeutic composition for the treatment, alleviation or prophylaxis of autoimmune conditions.

Autoimmunity is present to some extent in everyone and is usually harmless. However, autoimmunity can cause a broad range of human illnesses, known collectively as autoimmune diseases, disorders or conditions. Autoimmune conditions occur when there is progression from benign autoimmunity to pathogenic autoimmunity when a misdirected immune response occurs in an individual in which the immune system attacks the body itself rather than a foreign body or a xenobiotic or other foreign compound or moiety. This progression is determined by genetic influences as well as by environmental triggers.

Immune reactions are nearly always characterised by inflammation, which indicates an underlying repair process. However, in the case of autoimmune conditions or diseases the inflammation may be chronic, causing tissue damage. For example, in rheumatoid arthritis chronic inflammation causes characteristic damage to joints and to cartilage. The precise origin and pathophysiological processes of these diseases are not fully known.

Current treatments for autoimmune conditions are generally concerned with pain management, the administration of anti-inflammatory drugs, replacing lost substance (for example, the provision of insulin in diabetes mellitus) or the administration of one or more immunosuppressants. These treatments are generally systemic rather than local and as such may cause adverse effects elsewhere in the body.

While these approaches may temporarily alleviate the conditions, or reduce their progress, they often act to directly counteract the actual physical state or effect rather than to remove, reduce or alter the underlying cause or aetiology of the condition. For example, it is known that many autoimmune reactions involve a T-cell mediated response, it would therefore be beneficial to provide a treatment for autoimmune conditions which acts on this response.

Autoimmunity is evidenced by the presence of autoantibodies (antibodies directed against the body) and T-cells which are reactive with host antigens. Autoimmune conditions may be systemic, for example systemic lupus erythematosus, or organ specific, for example thyroiditis. Other examples of autoimmune conditions include Sjögren's syndrome, Hashimoto's thyroiditis, Myasthenia gravis, rheumatoid arthritis, juvenile (type 1) diabetes, polymyositis, scieroderma, Addison's disease, vitiligo, pernicious anaemia, glomerulonephritis, and pulmonary fibrosis.

It is an object of the present invention to provide a therapeutic composition which mediates an effect on an autoimmune condition by acting on the underlying cause or causes of the condition. However, the present invention may additionally have an effect on the physical state or effect of the condition.

Accordingly, the present invention provides a therapeutic composition for autoimmune conditions, the composition comprising an enzyme and an immunogen at a dose which provides a beneficial effect in an individual in need of treatment.

Advantageously, the composition of the present invention mediates a response which acts on or affects the underlying cause of the autoimmune condition. For example, it may act to downregulate T-cell mediated reactions. Without wishing to be bound by theory, the present inventor believes that the immunogens of the present invention indirectly reduce T-cell activity by means of an action mediated via the Langerhans or the dendritic cells or by the thymus, which action redirects antigen sensitive lymphocytes towards regulatory function (e.g. IL-10 production) or redirects cell activity away from the target site of the immunogen.

The term "immunogen" as used herein is intended to define any substance capable of inducing an immune response. It is not intended that any of the properties of the immunogen, such as molecular weight, are to be restricted by this term.

In the description which follows, the present invention will be described with particular reference to the treatment of rheumatoid arthritis. However, the invention finds equal utility in the treatment of other disorders by the selection of an appropriate immunogen. For example, multiple sclerosis may be treated by the use of myelin basic protein as the immunogen, thyroiditis or Hashimoto's disease may be treated using thyroid proteins as the immunogen, and diabetes mellitus may be treated using insulin or β-cell proteins as the immunogen. Additionally, mixtures or combinations of immunogens may be used, especially where a condition implicates or is associated with one or more immunogens.

Preferably, the enzyme used in the composition is a liver enzyme or a mucopolysaccharidase. More preferably, the enzyme is a glucuronidase and most preferably is β-glucuronidase. Ideally, the β-glucuronidase is β-D-glucuronoside glucuronosohydrolase (Registry number EC 3.2.1.31). The source of the enzyme has been found to make no difference to the activity of the composition, provided that the enzyme is free from preservatives or sorbitol. Hence, it may be necessary to purify the enzyme to enable its use in the composition of the invention. Any method of purification may be used but it has been found to be convenient to use gel filtration chromatography or tangential flow filtration.

It is preferred that the enzyme is purified to a concentration of at least 20,000 Fishman units/mg and is present in the composition at a concentration of between 200 and 10,000 units/ml and ideally between 1,000 and 5,000 units/ml.

It has been found that contamination by other proteins, even at very low levels can affect the activity of the enzyme. It is therefore preferred that a stabiliser and/or activator is present in the composition. The stabiliser and/or activator is preferably an inert proteinaceous moiety, for example protamine sulphate or 1,10 diamino decane. Preferably, the stabiliser and/or activator is present at a concentration of up to 20 mg/l. Where the stabiliser and/or activator is protamine sulphate, it is preferably present at a concentration of between 1 and 10 mg/l, more preferably at a concentration of between 3 and 9 mg/l and ideally at about 6 mg/l (equivalent to 6 µg/ml).

The composition may further comprise hydroxyl moieties. Preferably, the hydroxyl moieties are provided by polyols which contain at least two hydroxyl moieties and more preferably by sugars or diols which contain at least two hydroxyl moieties. The preferred source of the hydroxyl moieties is 1,3 cyclohexane diol. Preferably, the 1,3 cyclohexane diol is present at a concentration of up to 20 µg/l, more preferably the 1,3 cyclohexane diol is present at a concentration of between 0.1 and 10 µg/l and ideally at a concentration of 1 µg/l. The stereochemistry of the 1,3 cyclohexane diol has been found not to adversely affect the present invention and hence either the cis, or trans forms or a racemic mixture may be used.

The composition is preferably buffered to neutral or an acid pH. More preferably, the composition is buffered to a pH of between 5 and 6.5 and ideally the composition is buffered to pH 5.9.

In the preferred embodiment of the invention where the composition is used in the treatment of rheumatoid arthritis the preferred immunogen is collagen or fragments, derivatives, conjugates, mimetics or other products thereof or which have a collagen-type structure or activity whether natural, synthetic or modified, regardless of source. The term "collagen" as used hereafter is intended to include such collagen products as above described. The collagen is preferably present in a solution. The collagen may be from any source but it is preferred that the collagen be free from preservatives or sorbitol or other additives. Hence, it may be necessary to purify the collagen to enable its use in the composition of the invention. Any method of purification may be used but it has been found to be convenient to use gel filtration chromatography or tangential flow filtration.

The concentration of collagen present in the composition may be of between 10 and $1 \times 10^{15}$ molecules/ml. More preferably, the collagen present in the composition may be at a concentration of between $1 \times 10^4$ and $1 \times 10^{13}$ molecules/ml. Generally, the concentration of the collagen present in the composition will vary according to the dose required, it is therefore contemplated that three ranges of collagen dosed compositions will be made available, these will be vary in strength from high to low. Compositions in the high strength range will contain collagen at a concentration of the order of $1 \times 10^{10}$ to $1 \times 10^{15}$ molecules/ml, and more preferably will contain about $1 \times 10^{12}$ to $1 \times 10^{13}$ molecules/ml. Ideally the high strength composition will contain $2.5 \times 10^{13}$ molecules/ml. For compositions in the mid-strength range, collagen will preferably be present at a concentration of the order of $1 \times 10^9$ to $1 \times 10^{13}$ molecules/ml, and more preferably will contain about $1 \times 10^{10}$ to $1 \times 10^{12}$ molecules/ml. Ideally the mid-strength composition will contain $2.5 \times 10^{11}$ molecules/ml. For compositions in the low strength range, collagen will preferably be present at a concentration of the order of $1 \times 10^2$ to $1 \times 10^8$ molecules/ml, and more preferably will contain about $1 \times 10^4$ to $1 \times 10^7$ molecules/ml. Ideally the mid-strength composition will contain $2.5 \times 10^5$ molecules/ml.

Preferably, the composition further comprises a glycosaminoglycan or mixtures or combinations thereof. Any glycosaminoglycan can be used but it is preferred that the glycosaminoglycan be selected from the group comprising hyaluronate (D glucuronic acid N acetyl D glucosamine), chondroitin sulphate (D glucuronic acid N acetyl D galactosamine 1, 3, 4 or 6 sulphate), dermatan sulphate (D glucuronic acid or L iduronic acid N acetyl D galactosamine), keratan sulphate (D galactose N acetyl D glucosamine sulphate), and heparan sulphate (D glucuronic acid or L iduronic acid N acetyl D glucosamine). The most preferred glycosaminoglycan is chondroitin-6-sulphate.

A preferred embodiment is a composition comprising 1,000 to 5,000 Fishman units/ml β-glucuronidase, 6 µg/ml protamine sulphate, 1 µg/ml 1,3 cyclohexane diol, and 0.5 mg/ml chondroitin sulphate, and collagen present in a concentration selected from the group consisting of $2.5 \times 10^{12}$, $2.5 \times 10^{10}$ and $2.5 \times 10^4$ molecules/ml buffered to a pH of 5.9.

The glycosaminoglycan is preferably present in the composition at a concentration of between 0.1 and 1.0 mg/ml, most preferably 0.5 mg/ml. Ideally the glycosaminoglycan is free from preservatives or sugars and to ensure this it may be necessary to purify the glycosaminoglycan before use. Convenient methods of purification include gel filtration chromatography or tangential flow filtration.

The composition of the invention may be administered in any conventional manner either systemically or locally, for example by oral-, parenteral-, intra-dermal-, topical-, rectal-, nasal- routes, by local injection or by transdermal infusion. At present it is preferred that the composition is administered by sub-cutaneous injection, preferably by intradermal injection, or as any form of trans-dermal infusion. It is not necessary for the composition to be administered locally to the region of autoimmunity, especially in rheumatoid arthritis, but it may be preferable to do so in other conditions in order to minimise any contra-indications or to expedite an effect at a particular location.

In a preferred embodiment, the composition is prepared a short time before administration or even immediately prior to administration. In this embodiment the composition may be provided as two preparations, an enzyme preparation and a collagen preparation, which are introduced to one another and mixed prior to administration. In this embodiment, the enzyme solution contains the stabilised enzyme, the hydroxyl moiety and the enzyme in a buffered solution; all of which are present as described above. The collagen solution contains the collagen and the glycosaminoglycan, buffered as described above. Preferably, the composition as administered contains more collagen solution than enzyme solution, more preferably at least twice the amount of collagen solution (by volume) and ideally about 4 parts collagen solution to each part enzyme solution, by volume.

Accordingly, the present invention also provides a kit for preparing the composition of the invention, the kit comprising an enzyme solution and an immunogen solution, the two solutions being introduced to one another and allowed to admix prior to administration to an individual in need of treatment. The kit may be presented in the form of a multi-chambered or multi-barrelled dispenser such as a syringe.

The composition of the present invention may preserved between formation and use. For example, the composition may be frozen, dried, freeze-dried, lyophilized, encapsulated or further preserved with a suitable chosen preservative which has little or no adverse effect on the in vivo activity of the composition or by any other preserving technique commonly used or known for pharmaceuticals. Where the composition is dried or freeze-dried or otherwise rendered solid, the composition may be formed into a tablet, capsule, lozenge or other solid dosage form for oral administration or reconstituted for use in a solution or liquid form, for example for injection. Where the composition is frozen, it may be convenient to freeze the composition or its components in dose unit amounts, optionally in a syringe, to facilitate use by the individual or medical practitioner.

Any pharmaceutically acceptable solvent may be used to produce the liquid form of the composition. Similarly, the usual binders, excipients, vehicles, and other standard dosage additives may be used in the composition of the invention.

The present invention also provides a method of treating or preventing autoimmune conditions, the method comprising the administration of a therapeutically effective amount of a composition comprising an enzyme and an immunogen to an individual in need of treatment.

The present invention further provides a method of treating, alleviating or preventing rheumatoid arthritis, the method comprising the administration of a therapeutically effective amount of a composition comprising β-glucuronidase and collagen to an individual in need of treatment.

The present invention also provides the use of a therapeutically effective amount of an enzyme and an immunogen in the preparation of a medicament for the treatment or prevention of autoimmune conditions.

In a further aspect the present invention also provides the use of a β-glucuronidase and collagen in the preparation of a medicament for the treatment of rheumatoid arthritis.

In a final embodiment, the present invention provides a composition comprising 0.5-2.5 mg/ml β-glucuronidase, 6 µg/ml protamine sulphate, 1 µg/ml 1,3 cyclohexane diol, and 0.5 mg/ml chondroitin sulphate, buffered to pH 5.9 and further comprising either $2.5 \times 10^{13}$, $2.5 \times 10^{11}$ or $2.5 \times 10^{5}$ molecules/ml of collagen for use in the treatment of rheumatoid arthritis.

Embodiments of the invention will now be described, by way of example only, with reference to the following accompanying drawings, of which:—

EXAMPLE 1

Figure 1:
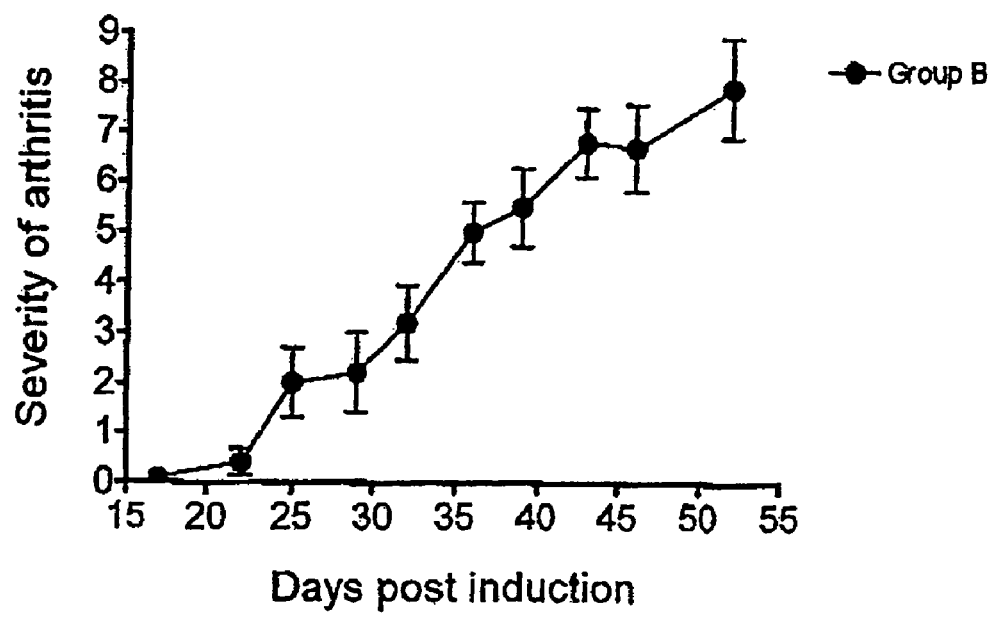
FIG. 1 is a graph showing the course of arthritis in the control group (Group B).

β-glucuronidase (EC 3.2.1.31) (obtained from the marine mollusc *Haliotis midee* (South African abalone) was purified by gel filtration chromatography to remove any preservatives or sorbitol present.

The purified β-glucuronidase was added to a buffered solution at pH 5.9 to give a final concentration of 1.5 mg/ml. 1,3 cyclohexane diol (Sigma, Poole, Dorset, UK) was added to a final concentration of 1 µg/ml. Protamine sulphate BP was added, with stirring to prevent precipitation, to a final concentration of 6 µg/ml.

Separately, natural collagen-type II was purified by gel filtration chromatography to remove any preservatives or sorbitol present.

The purified collagen was dissolved in a solution and buffered to pH 5.9 to give a final collagen concentration of $2.5 \times 10^{13}$. To this solution, chondroitin sulphate was added to give a final concentration of 0.5 mg/ml.

0.01 ml of enzyme solution was introduced to 0.04 ml of collagen solution and allowed to mix. The 0.05 ml bolus of composition was used as an intradermal injection in an arthritis model in mouse. Paw weights and volumes were measured against control mice receiving vehicle only, collagen only or β-glucuronidase only.

EXAMPLE 2

Effects of β-glucuronidase/type II Collagen on Collagen-Induced Arthritis in the DBA/1 Mouse Location The test samples were prepared by McEwen Laboratories Ltd. Pangbourne, Berkshire, England. The test facility was at the Department of Pathology and Microbiology, School of Medical Sciences, University of Bristol, England.

Study Schedule

The study schedule was as follows:
Study initiation date $2^{nd}$ Feb. 2004
Assay completion date $24^{th}$ Mar. 2004

Objective of Study:

The study was designed to determine the effects of two test doses of type II collagen in combination with β-glucuronidase on the incidence and severity of collagen-induced arthritis. Male DBA/1 mice were chosen for the study and arthritis was initiated using type II collagen (chicken) in complete Freunds adjuvant as the initiating stimulus. Treatments were provided as separate samples of type II collagen and β-glucuronidase, Samples were kept at 4° C. and were mixed immediately prior to injection. Treatment was given as a single dose injected subcutaneously into the scruff of the neck on day 10 post-induction. Animals were scored for clinical arthritis from day 17 to day 52 twice weekly by observation of joint redness and swelling. The study centre was blinded.

Materials and Methods

Mice

Thirty male DBA/1 mice were obtained from Harlan Olac at 6 weeks of age. The animals were maintained in the animal house of The School of Medical Sciences, University of Bristol, until they had reached 12 weeks of age before the study was initiated. On day 0 all mice were given 100 µg chicken type II collagen emulsified into complete Freund's adjuvant (CII/CFA) by injection at the base of the tail. Treatments were given by subcutaneous injection to the scruff of the neck on day 10 and then clinical joint swelling was scored twice weekly from day 17 to 52.

Treatment

β-glucuronidase (E.C. 3.2.1.31) (obtained from the marine mollusc *Haliotis midae*) was provided as a freeze-dried powder. This was further purified (to remove any sorbitol and salts used in the freeze drying process or as stabilisers) by size exclusion (gel filtration) chromatography and diluted to a concentration of 2 mg/ml in a buffer pH5.9. To this solution was added $1 \times 10^{-8}$ mg/ml of 1,3-cycolhexane diol and $6 \times 10^{-5}$ mg/ml of protamine sulphate. This solution was then aseptically filled into vials and stored between 2° C. and 8° C. until use.

Type II collagen (obtained from chicken cartilage) was provided as a freeze-dried powder and was further purified as above by gel filtration chromatography. This was then diluted in a buffer solution pH5.9 containing 0.5 mg/ml chondroitin sulphate (purified from sharks' cartilage). Two dilutions were used representing approximately 50 ng/ml and 50 fg/ml and these were separately dispensed aseptically into vials and stored at 2° C. to 8° C. until use.

Treatments were provided by McEwen Laboratories Ltd and labelled as follows.

1. Enzyme A . . . β-glucuronidase solution as described above
2. CII A . . . Collagen 50 fg/ml as described above
3. Enzyme B . . . Buffer control
4. CII B . . . Buffer control
5. Enzyme C . . . β-glucuronidase solution as described above
6. CII C . . . Collagen 50 ng/ml as described above The identity of the samples was recorded by McEwen Laboratories but not disclosed to the University of Bristol in advance of the end of the in life phase. A, B and C samples were mixed in a 1ml syringe no longer than 10 minutes prior to injection of 200 µl into each animal. Samples were stored at 4° C. until use, and kept on ice following removal from the refrigerator and up to the point of injection.

Experimental Groups (n=10/Group)
Group A: day 0 CII/CFA, day 10 treatment with mixture A
Group B: day 0 CII/CFA, day 10 treatment with mixture B
Group C: day 0 CII/CFA, day 10 treatment with mixture C Endpoints Clinical score of joint swelling. Animals were inspected twice weekly from day 17 to day 52. On each occasion, each of the four limbs was given a score according to (0=normal; 1=slight swelling of whole joint or individual digit inflammation; 2=intermediate swelling of whole joint with redness and/or inflammation in more than one digit; 3=moderate joint inflammation and redness spreading to multiple digits, some signs of bone remodelling; 4=severe joint inflammation and redness spreading to multiple digits, overt signs of bone remodelling.

Results

Sample decoding. The identity of the treatment samples was revealed to the study centre following necropsy.

Disease was present in the control group (B) with the expected incidence and severity for this model. Disease was present at very low level on the first day of inspection, day 17, but the incidence and severity increased from that day until the end of the in-life phase (FIG. 1). This progression is in keeping with the expected course of arthritis in this model. The overall disease levels in the control group were severe compared to many similar experiments carried out in the test facility.

Figure 2:
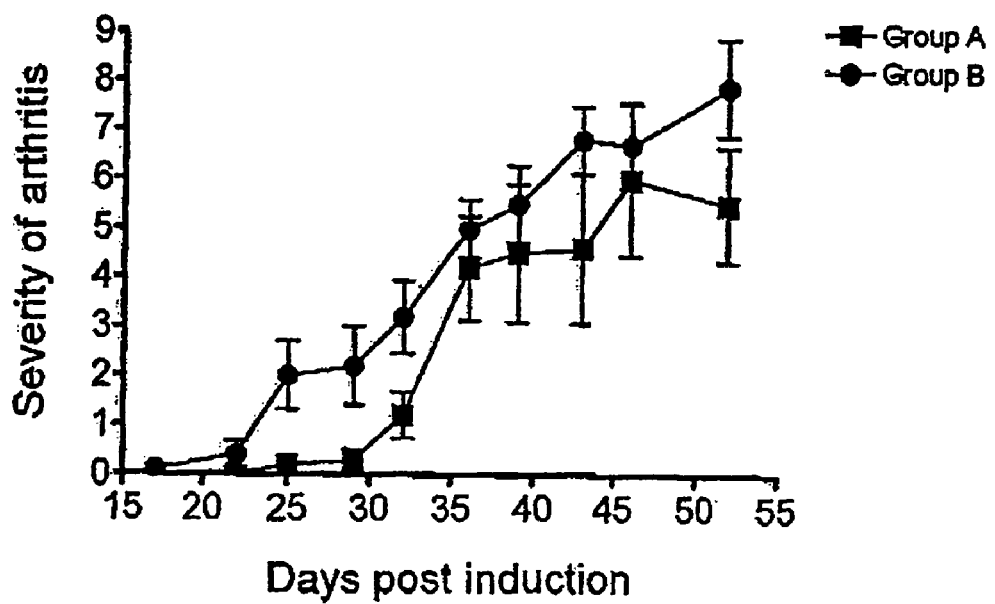
FIG. 2 is a graph showing a comparison of the course of disease between Group A and Group B over time.
Figure 3:
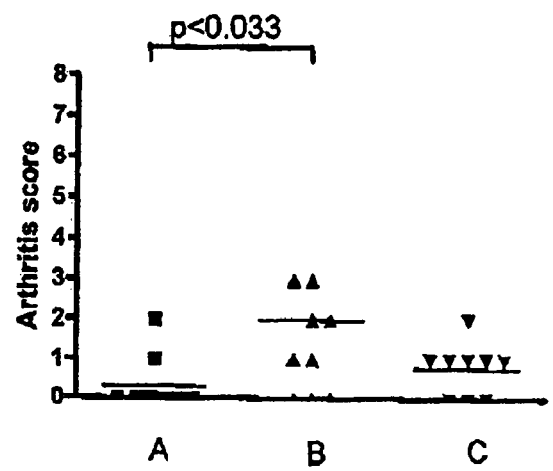
FIG. 3 shows severity of arthritis in each of the experimental groups A, B and C on day 29.

Disease in the low dose treatment group was delayed in onset compared to the controls (FIG. 2). This meant that a single point T test revealed a significant difference between severity of arthritis between Group A and Group B as tested on day 29 (FIG. 3). Thereafter, disease severity increased in Group A. Although it remained reduced when compared to Group B for the duration of the experiment, the overall curve indicated no significant effect of treatment beyond day 29.

Figure 4:
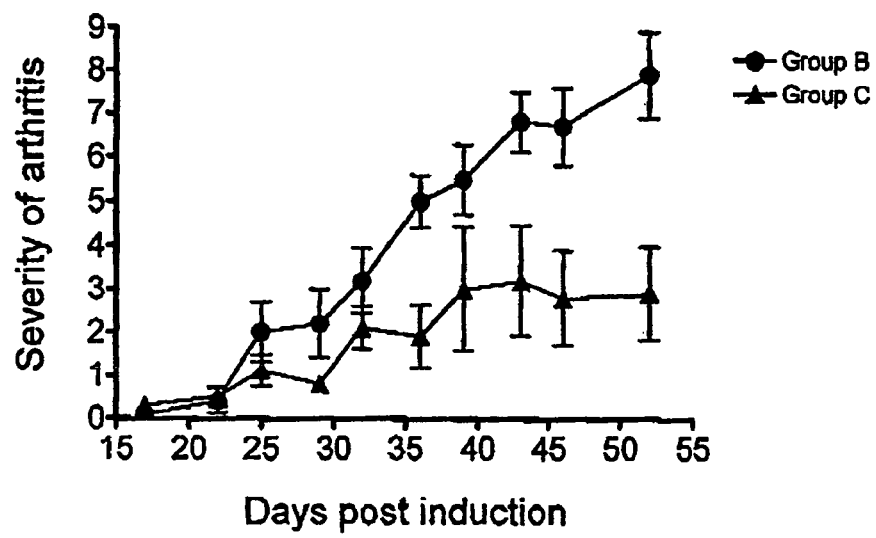
FIG. 4 is a graph showing a comparison of the course of disease between Group B and Group C over time.
Figure 5:
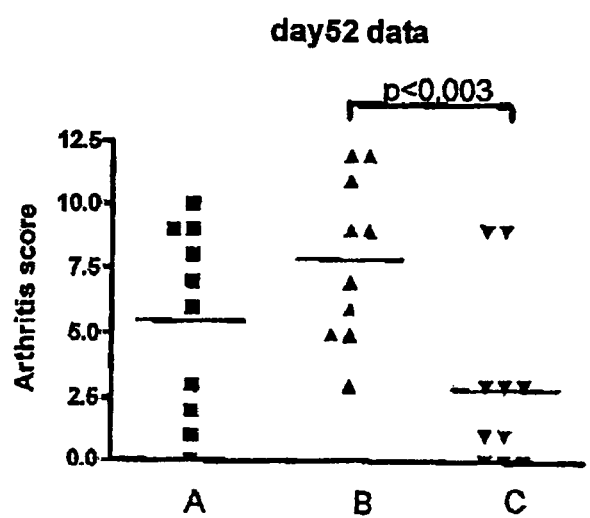
FIG. 5 shows severity of arthritis in each of the experimental groups A, B and C on day 52 and indicates that high dose treatment significantly reduced peak arthritis score.

Disease in the high dose treatment group was lower than that in Group B from day 25 to the end of the experiment (FIG. 4). Disease in Group C did not follow the normal course for arthritis in this model, disease affected a lower than normal number of animals for the majority of the experiment, and the severity of the group as a whole was very much lower than expected. With the exception of two animals, disease severity in Group C remained extremely low. The lack of protection in these two animals meant that the variance in the Group C data set was relatively high. However, the severity of arthritis was significantly lower when comparing Group C to Group B on days 42, 46 and 52 (Mann-Whitney U test). The data for day 52 (as the day on which highest disease was scored) are shown in FIG. 5. In addition, Annova analysis with Kruskal Wallis post-test reveals an overall significant difference in the level of disease in Group C compared to Group B (p=0.0196).

CONCLUSIONS

Both treatment doses altered the course of arthritis in the experiment. The much less marked reduction, which appeared as a delay on progression, with low dose treatment was significant within the experiment. The alteration to the course of disease observed following high dose treatment is suggestive of a potent anti-arthritic effect. The levels of disease reduction in Group C are within the range seen when established anti-arthritic drugs are given during the course of similar experiments. The fact that this level of protection was observed following a single treatment is highly encouraging. Improvement of treatment levels with the low dose may be achieved by given further doses as disease progresses.

What is claimed is:

1. A therapeutic composition for the treatment of rheumatoid arthritis, wherein the composition comprises purified beta-glucuronidase at a concentration of between 200 and 10,000 Fishman units/ml and purified collagen at a concentration of between 0.5 and 2.5 mg/ml, wherein the composition is at a dose that provides a beneficial effect to an individual in need of treatment of rheumatoid arthritis.

2. The composition of claim 1, wherein the beta-glucuronidase is beta-D-glucuronoside glucuronosohydrolase (EC 3.2.1.31).

3. The composition of claim 1, further comprising protamine sulphate or 1,10-diamino decane.

4. The composition of claim 3, wherein the protamine sulphate or 1,10-diamino decane is present at a concentration of 3-9 mg/L.

5. The composition of claim 1, wherein the composition is buffered to an acid or neutral pH.

6. The composition of claim 5, wherein the composition is buffered to a pH of between 5 and 6.

7. The composition of claim 1, wherein the composition further comprises a glycosaminoglycan.

8. The composition according to claim 7, wherein the glycosaminoglycan is selected from the group consisting of hyaluronate, chondroitin sulphate, dermatan sulphate, keratan sulphate and heparan sulphate.

9. The composition of claim 8, wherein the hyaluronate is D-glucuronic-acid-N-acetyl-D-glucosamine; the chondritin sulphate is D-glucuronic acid-N-acetyl-D-galactosamine 4- or 6-sulphate; the dermatan sulphate is D-glucuronic acid or L iduronic acid N-acetyl-D-galactosamine; the keratan sulphate is D-galactose-N-acetyl-D-glucosamine sulphate; and the heparan sulphate is D-glucuronic acid or L-iduronic acid N-acetyl-D-glucosamine.

10. The composition of claim 7, wherein the glycosaminoglycan is chondroin-6-sulphate.

11. The composition of claim 7, wherein the glycosaminoglycan is present at a concentration of between 0.1 and 1.0 mg/ml.

12. The composition of claim 1, wherein the composition is in a formulation suitable for transdermal infusion or intradermal injection.

13. A therapeutic composition for the treatment of rheumatoid arthritis, the composition comprising a purified beta-glucuronidase at a concentration of between 200 and 10,000 Fishman units/ml, purified collagen at a concentration of between 0.5 and 2.5 mg/ml, and 1,3 cyclohexane diol and either protamine sulphate or 1,10-diamino decane in which the beta-glucuronidase and the collagen are present in the composition at a dose which provides a beneficial effect to an individual in need of treatment rheumatoid arthritis.

14. The composition of claim 13, wherein the protamine sulphate or 1,10 diamino-decane is present at a concentration of 3-9 μg/ml and the cyclohexane diol is present at a concentration of 1 μg/ml.

15. A composition for the treatment of rheumatoid arthritis comprising 1,000 to 5,000 Fishman units/ml β-glucuronidase, 6 μg/ml protamine sulphate, 1 μg/ml 1,3 cyclohexane diol, and 0.5 mg/ml chondroitin sulphate and collagen present in a concentration selected from the group consisting of $2.5 \times 10^{12}$, $2.5 \times 10^{10}$ and $2.5 \times 10^{4}$ molecules/ml buffered to a pH of 5.9.

16. A method for the treatment of rheumatoid arthritis comprising administering by transdermal infusion or intradermal injection an effective amount of a composition of claim 1, 13 or 15 to ameliorate a symptom of rheumatoid arthritis to an individual in need thereof.

* * * * *

UNITED STATES PATENT AND TRADEMARK OFFICE
CERTIFICATE OF CORRECTION

PATENT NO. : 7,901,676 B2  Page 1 of 1
APPLICATION NO. : 10/820099
DATED : March 8, 2011
INVENTOR(S) : Simon McEwen It is certified that error appears in the above-identified patent and that said Letters Patent is hereby corrected as shown below:

On the Title page: item (73), should read:

~~Epidyme Limited, Berkshire (GB)~~ McEwen Laboratories, Ltd., Berkshire (GB)

Signed and Sealed this
Twelfth Day of July, 2011

David J. Kappos
*Director of the United States Patent and Trademark Office*